(12) United States Patent
Block et al.

(10) Patent No.: US 8,933,133 B2
(45) Date of Patent: Jan. 13, 2015

(54) ANIMAL FEEDS CONTAINING POLYOLS

(75) Inventors: Stephanie S. Block, Decatur, IN (US); Perry H. Doane, Decatur, IN (US)

(73) Assignee: ADM Alliance Nutrition, Inc., Decatur, IL (US)

( * ) Notice: Subject to any disclaimer, the term of this patent is extended or adjusted under 35 U.S.C. 154(b) by 1432 days.

(21) Appl. No.: 11/956,886

(22) Filed: Dec. 14, 2007

(65) Prior Publication Data

US 2008/0146520 A1 Jun. 19, 2008

Related U.S. Application Data

(60) Provisional application No. 60/869,990, filed on Dec. 14, 2006.

(51) Int. Cl.
| | | |
|---|---|---|
| *A23K 1/18* | (2006.01) | |
| *A61K 31/77* | (2006.01) | |
| *A23K 1/16* | (2006.01) | |

(52) U.S. Cl.
CPC .............. *A23K 1/1609* (2013.01); *A23K 1/1813* (2013.01); *A23K 1/184* (2013.01)
USPC ........................................... 514/772.3; 426/2

(58) Field of Classification Search
CPC ......... A23L 1/097; A61K 31/77; C08L 71/02
USPC ........................................... 514/772.3; 426/2
See application file for complete search history.

(56) References Cited

U.S. PATENT DOCUMENTS

| | | | |
|---|---|---|---|
| 3,338,718 A | | 8/1967 | Olsen et al. |
| 4,086,279 A | * | 4/1978 | Langdon et al. ............. 568/623 |
| 4,127,676 A | | 11/1978 | Merensalmi |
| 4,528,199 A | * | 7/1985 | Moon et al. ...................... 426/53 |
| 4,564,692 A | * | 1/1986 | Feldmann et al. ............ 549/464 |
| 5,601,836 A | | 2/1997 | Parker |
| 5,824,322 A | * | 10/1998 | Balasubramanian ...... 424/280.1 |
| 6,007,848 A | * | 12/1999 | Hendrick et al. .................. 426/3 |
| 6,221,381 B1 | * | 4/2001 | Shelford et al. .............. 424/442 |
| 6,440,447 B1 | | 8/2002 | Luhman |
| 6,455,083 B1 | | 9/2002 | Wang |
| 6,849,748 B2 | | 2/2005 | Moore et al. |
| 6,866,861 B1 | | 3/2005 | Luhman |
| 2004/0076659 A1 | | 4/2004 | Shelford et al. |
| 2004/0110994 A1 | * | 6/2004 | Bhatia ............................ 568/845 |
| 2004/0152907 A1 | | 8/2004 | Moore et al. |
| 2005/0204612 A1 | | 9/2005 | Connemann et al. |
| 2005/0249841 A1 | | 11/2005 | Hayek et al. |
| 2006/0116330 A1 | * | 6/2006 | Pitha et al. ....................... 514/23 |
| 2006/0204554 A1 | | 9/2006 | Cecava et al. |
| 2007/0209599 A1 | | 9/2007 | Block et al. |

FOREIGN PATENT DOCUMENTS

| | | |
|---|---|---|
| DE | 4213175 A1 | 10/1993 |
| GB | 2102268 A | 2/1983 |
| WO | WO 96/11585 | 4/1996 |
| WO | WO 97/03650 | 2/1997 |

OTHER PUBLICATIONS

Hoff et al. Southern Medical Journal, 1999, 92(7), p. 651-659.*
Wakita et al. British Journal of Nutrition, 1987, 58, p. 493-502.*
Waddell et al. Journal of Clinical Investigation, 1973, 52, p. 2725-2731.*
Baumgardt, BR. Jourmal of Animal Science, 1967, 26, p. 1186-1194.*
Krause et al. Journal of Animal Science, 1998, 76(11), p. 2912-2920.*
Halacheva et al., Macromolecules, 2006, 39, p. 6845-6852, Published on Web Aug. 31, 2006.*
Meyer et al., J. Anim. Sci., 1972, 34, p. 234-240.*
R.B. Johnson, "The Treatment of Ketosis with Glycerol and Propylene Glycol," *The Cornell Veterinarian*, vol. XLIV, D.W. Bruner, ed., Ithaca, NY 1954.
J.M. Defrain, et al., "Feeding Glycerol to Transition Dairy Cows: Effects on Blood Metabolites and Lactation Performance," *Journal of Dairy Science*, 87:4195-4206, 2004.
L.J. Fisher et al., "Preliminary Evaluation of the Addition of Glucogenic Materials to the Rations of Lactating Cows," *Canadian Journal of Animal Science*, 51: 721-727, 1971.
H.K. Goering and P.J. Van Soest, "Forage Fiber Analyses (Apparatus, Reagents, Procedures, and Some Applications)" *Agric. Handbook*, No. 379, ARS-USDA, Washington, DC, 1970.
J.K. Drackley, "Biology of Dairy Cows During the Transition Period: the Final Frontier?," *Journal of Dairy Science*, 82: 2259-2273, 1999.
S. Murdan et al., "Water-in-sorbitan Monostearate Organogels (Water-In-Oil Gels)," *Journal of Pharmaceutical Sciences*, Jun. 1999:88(6), 615-619.

* cited by examiner

*Primary Examiner* — Layla Bland
*Assistant Examiner* — Jonathan S Lau
(74) *Attorney, Agent, or Firm* — Andrew F. Nilles (57) ABSTRACT

Animal feed compositions which include a polyol are described. Processes for producing an animal feed composition with a polyol are disclosed. Methods of feeding an animal the polyol are also disclosed.

16 Claims, 3 Drawing Sheets

Fig. 1  Evaluation of Sorbitan and Polyglycerol

ANIMAL FEEDS CONTAINING POLYOLS

CROSS REFERENCE TO RELATED APPLICATIONS

The application claims the priority benefit of U.S. Provisional Patent Application No. 60/869,990, filed Dec. 14, 2006, the disclosure of the entirety of which is incorporated by this reference.

FIELD OF DISCLOSURE

The present disclosure relates to animal feeds which comprise at least one polyol ingredient. Processes for producing animal feeds and methods of feeding animals are also disclosed.

BACKGROUND

At certain times, commercial animals, such as, for example, livestock and/or domestic pets may not be able to readily meet their nutritional requirements by normal means. For example, during periods of stress the animal's digestive efficiency and/or amount of feed consumed may be reduced. As a result, overall productivity may be reduced. The reduced productivity may also have consequences on the economics of a livestock production facility and/or the overall health of the animals.

Stress to an animal can result from a variety of factors, such as, for example, changes in environment, feed, or health. For example, during pregnancy and/or the period around parturition (up to 4 weeks prior to and 8 weeks post birth), the animal undergoes a rapid and extensive adjustment in metabolic and productive demands. Other periods of stress may include times of nutrient shortfall, illness, changes in social environment, and changes in environmental conditions, for example, changes in location, transportation, increases or decreases in temperature or other changes in weather conditions (such as, for example, increased humidity or storms), and changes in feed composition or feeding patterns. During these periods of stress, the animal may not consume sufficient nutrients for an energy balance. As used herein, the term "energy balance" includes a balance where the energy associated with the animal's dietary consumption is substantially equal to the energy expenditures by the animal. As used herein, the term "energy imbalance" includes where the energy associated with the animal's dietary consumption is less than the energy expenditures by the animal.

Animals, including ruminants, rely heavily on sugar carbohydrates predominantly for the function of cellular metabolism, including, for example in the liver and the mammary glands. However, in ruminants fed carbohydrates, such as glucose, the carbohydrates are fermented by the rumen microflora, and no considerable amount of the simple sugars pass through the rumen into the post-rumen portion of the digestive tract intact. As a result, the ruminants must produce intact glucose in the liver to support the carbohydrate needs of the animal. Under normal conditions, the liver may provide the required amounts of carbohydrates. However, in times of stress an energy imbalance may develop.

For example, bovines, such as, dairy cattle and beef cattle, may have a negative energy balance in the period surrounding calving. Other livestock, such as, porcines, equines, ovines, caprines, and others may also suffer from negative energy balances during pregnancy and the period immediately afterwards (i.e., during lactation). As used herein, the term "negative energy balance" is synonymous with "energy imbalance" and refers to when the energy intake associated with the animal's dietary consumption is less than the amount of energy expended by the animal. This energy imbalance may begin during times of stress, such as, immediately prior to parturition and may persist through the first several weeks of lactation. During this period, dietary intake may be insufficient to supply the energy needed to meet the nutritional requirements associated with the rapidly rising production of milk. Large metabolic adjustments are required to support birth, recovery, and milk production, and productive and health concerns may arise in response to the metabolic demands.

Lack of sufficient nutrition prior to and after birth may result in extensive mobilization of body reserves of the mother, such as release or production of free fatty acids, to continue support for milk production. Fatty acid mobilization may exceed the capacity of the liver to process the fatty acids into energy sources, such as acetyl CoA and ketones, which may result in fat accumulation in the liver. This fat accumulation may further inhibit glucose production in the liver, further exacerbating the underlying energy deficit. This compounding problem may limit milk production and/or may impact health via a variety of metabolic disorders.

One approach to alleviate some of the immediate energy demands and metabolic derangement for animals near the time of birthing, such as, for example, cattle prior to, during, and after calving, may involve feed additives such as propylene glycol and calcium propionate being dosed or fed in the diet. However, these compounds may have management limitations from a producer's perspective. In addition, to be metabolically effective in bovines and/or other ruminants, substantial amounts of the glucose precursors must make it to the small intestine, for example, by making it through the rumen substantially intact. However, because intake is limited and the rumen fermentation process may still be adjusting to the increased energy density and demands, it may not be feasible to merely increase the amount of energy dense feed supplied to the animal. Starch or fat, as energy sources, used in excess within the diet may present problems for the rumen fermentation and place the animal at risk as well.

Further, in ruminants the amount of these glucose precursors that escapes fermentation in the rumen is variable and may potentially be affected by microbial adaptation. This may require that greater amounts of these compounds be fed to the animal in order to elicit a comparable response.

Sugar alcohols have been used in ruminant feed to enhance milk production. In U.S. Pat. No. 4,127,676 to Merensalmi, a fodder additive for ruminants comprising at least one sugar alcohol having five or six hydroxyl groups is disclosed. In U.S. Pat. No. 6,440,447 to Luhman, a method for enhancing milk production by a ruminant comprising feeding the ruminant a feed that contains sorbitol is disclosed. Monomeric glycerol has also been utilized as a glucose precursor both to affect metabolism (R. B. Johnson, "The Treatment of Ketosis with Glycerol and Propylene Glycol," in *The Cornell Veterinarian*, Volume XLIV, D. W. Bruner, ed., Ithaca, N.Y., 1954) and to improve energy status (see, for example, J. M. DeFrain, et al., "Feeding Glycerol to Transition Dairy Cows: Effects on Blood Metabolites and Lactation Performance," *J. Dairy Sci.* 87:4195-4206, 2004 and L. J. Fisher et al., "Preliminary Evaluation of the Addition of Glucogenic Materials to the Rations of Lactating Cows," *Can. J. Anim. Sci.,* 51:721-727, 1971).

Sugar alcohols and glycerol may provide some energy to a ruminant or mono-gastric animal. Unabsorbed polyalcohols may also create an osmotic effect increasing rate of fecal movement and reducing constipation. As used herein, the term "sugar alcohol" includes carbohydrate residues in open chain form in which the carbonyl functional group of the carbohydrate has been reduced to a hydroxyl group. As used herein, the term "glycerol" includes ethylene glycol, propylene glycol, and glycerol. However, the amount of compound escaping rumen fermentation or being digested may be variable and may require increased amounts of the sugar alcohol or glycerol in order to pass to the intestinal tract. In addition, the hydroscopic nature of these materials may present manufacturing challenges in some feed applications.

Thus, there remains a demand for feed ingredient compounds that exhibit the ability to supply carbohydrate and glucose precursors in the intestinal tract of the animals. Further, there remains a demand for feed ingredient compounds that are resistant to fermentation in the rumen of ruminants and exhibit the ability to pass into the latter portions (i.e., post-rumen portions) of the ruminant digestive system where they can act as carbohydrate and glucose precursors, osmotic agents, and laxatives. The present disclosure addresses these problems and others and provides further advantages that one of ordinary skill in the art will readily discern from the detailed description that follows.

SUMMARY

Certain embodiments of the present disclosure relate to a feed composition comprising feed matter and an isolated or purified polyol selected from the group consisting of an anhydro-sugar alcohol, a polyglycerol, and combinations thereof. In certain embodiments the feed composition may be a ruminant feed composition.

Other embodiments relate to an animal feed composition wherein the anhydro-sugar alcohol is selected from the group consisting of sorbitan, isosorbide, and combinations of any thereof.

Other embodiments include a process for producing an animal feed composition. The process comprises mixing animal feed matter with an isolated or purified polyol selected from the group consisting of sorbitan, isosorbide, a polyglycerol, and combinations of any thereof to produce the animal feed composition. According to further embodiments of the process, the animal feed composition may be a ruminant feed composition and the isolated or purified polyol may further be an anhydro-sugar alcohol selected from the group consisting of anhydro-adonitol, anhydro-allitol, anhydro-altritol, anhydro-arabinitol, anhydro-ducitol, anhydro-erythritol, anhydro-galaxitol, anhydro-glucitol, anhydro-gulitol, anhydro-iditol, anhydro-inositol, anhydro-isomalt, anhydro-lactitol, anhydro-lyxitol, anhydro-maltitol, anhydro-mannitol, anhydro-perseitol, anhydro-ribitol, anhydro-rhamnitol, anhydro-talitol, anhydro-threitol, anhydro-xylitol, and combinations of any thereof. In other embodiments, the process may further comprise forming the composition into a form selected from the group consisting of a complete feed, a feed supplement, a feed additive, a premix, a top-dress, a tub, a mineral, a meal, a block, a pellet, a mash, a liquid supplement, and combinations of any thereof. In still other embodiments, the process may further comprise placing the composition in a container configured for shipping and associating indicia with the container, wherein the indicia is capable of directing a user on how to administer the composition to an animal.

Further embodiments of the disclosure relate to methods for feeding an animal. The methods comprise feeding an animal feed composition comprising an isolated or purified polyol selected from the group consisting of an anhydro-sugar alcohol, a polyglycerol, and combinations of any thereof, and animal feed matter to the animal.

Still further embodiments relate to methods of improving, increasing, offsetting, or counteracting impaired energy balance in an animal during a time of stress. The methods comprise feeding the animal a feed composition according to various embodiments described herein during a time of stress.

Other embodiments of the present disclosure relate to a feed composition comprising feed matter and an isolated or purified sorbitan, an isolated or purified polyglycerol, or a combination thereof. Upon administration of the animal feed composition, described herein, to a ruminant fed a restricted diet, a circulating level of non-esterified fatty acids in the ruminant's blood decreases after three hours.

DESCRIPTION OF THE DRAWINGS

The various embodiments of the present disclosure will be better understood when read in conjunction with the following figures.

DETAILED DESCRIPTION

Other than in the exemplary embodiments, or where otherwise indicated, all numbers recited herein expressing quantities of ingredients, reaction conditions and the like are to be understood as being modified in all instances by the term "about". Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, may inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

Any patent, publication, or other disclosure material, in whole or in part, that is identified herein is incorporated by reference herein but only to the extent that the incorporated material does not conflict with existing definitions, statements, or other disclosure material set forth in this disclosure. As such, and to the extent necessary, the disclosure as set forth herein supersedes any conflicting material incorporated herein by reference. Any material, or portion thereof, that is incorporated by reference herein, but which conflicts with existing definitions, statements, or other disclosure material set forth herein will only be incorporated to the extent that no conflict arises between that incorporated material and the existing disclosure material.

The present disclosure describes several different features and aspects of the invention with reference to various exemplary embodiments. It is understood, however, that the invention embraces numerous alternative embodiments, which may be accomplished by combining any of the different features, aspects, and embodiments described herein in any combination that one of ordinary skill in the art would find useful.

Various embodiments of the present disclosure include animal feed compositions comprising animal feed matter and an isolated or purified polyol. The polyols may be selected from the group consisting of a polyglycerol, anhydro-sugar alcohols, and combinations thereof. Other embodiments include processes for producing an animal feed composition. Still other embodiments include methods for feeding an animal and methods for stabilizing an energy balance of an animal during a time of stress.

As used herein, the term "sugar alcohol" includes carbohydrate residues in open chain form in which the carbonyl of the carbohydrate has been reduced to a hydroxyl group. As used herein, the term "anhydro-sugar alcohol" includes cyclic sugar alcohol residues containing at least one ring wherein the cyclic structure results from a dehydration of the parent sugar alcohol. The ring of the anhydro-sugar alcohol may be a 3-, 4-, 5-, 6-, or 7-membered cyclic ether. In certain embodiments, the ring of the anhydro-sugar alcohol may contain a 5- or 6-membered cyclic ether. According to other embodiments, the anhydro-sugar alcohol may contain two 5-membered fused cyclic ethers, for example, fused in a bicyclo [3.3.0] ring system. Anhydro-sugar alcohols may be made by any process known in the art.

The anhydro-sugar alcohols may be obtained commercially or prepared from starting materials by any method known in the industry. One non-limiting example of a process for producing an anhydro-sugar alcohol may comprise heating a pentitol or hexitol sugar alcohol starting material until molten, dehydrating the molten starting material in the presence of an acid catalyst to form an anhydro-sugar alcohol mixture, and purifying the anhydro-sugar alcohol from the anhydro-sugar alcohol mixture, for example, by distillation of the anhydro-sugar alcohol mixture in a first film evaporator. Certain embodiments of various approaches to the synthesis of anhydro-sugar alcohol are disclosed in greater detail in U.S. Pat. No. 6,849,748 to Moore et al. and U.S. Patent Application Publication No. 2004/0152907 to Moore et al., the disclosures of each are incorporated in their entirety by reference herein.

In one embodiment, the isolated or purified polyol may comprise a polyglycerol. As used herein, the term "polyglycerol" includes an oligomeric and/or polymeric chain composed of monomeric glycerol (i.e., $HOCH_2CH(OH)CH_2OH$) bonded together by ether linkages at the hydroxyl residue. The average number of glycerol monomer units in a particular polyglycerol may be represented by a number. For example, polyglycerol 4 contains, on average, 4 glycerol monomer units in the polymer chains. According to various embodiments, the isolated or purified polyglycerol polyol ingredients of the present disclosure may contain, on average, from 2 to 20 monomer glycerol units. That is, polyglycerols suitable for use in the present disclosure include polyglycerol 2 (PG2), polyglycerol 3 (PG3), polyglycerol 4 (PG4), polyglycerol 5 (PG5), polyglycerol 6 (PG6), polyglycerol 7 (PG7), polyglycerol 8 (PG8), polyglycerol 9 (PG9), polyglycerol 10 (PG10), polyglycerol 11 (PG11), polyglycerol 12 (PG12), polyglycerol 13 (PG13), polyglycerol 14 (PG14), polyglycerol 15 (PG15), polyglycerol 16 (PG16), polyglycerol 17 (PG17), polyglycerol 18 (PG18), polyglycerol 19 (PG19), polyglycerol 20 (PG20), and combinations of any thereof.

The glycerol feedstock for polyglycerol production may be obtained commercially or may be produced by any method known in the industry. For example, polyglycerols suitable for use in the compositions of the present disclosure may be commercially obtained from, for example, but not limited to, Gly-Tek of Twin Falls, Idaho; Abitec Corporation in Columbus, Ohio; Lonza Inc. in Allendale, N.J.; Solvay Polyglycerols in Houston, Tex.; and Stepan Company in Northfield, Ill. In one embodiment, the glycerol feedstock may be a co-product in the production of bio-diesel, such as, but not limited to, the process described in U.S. Patent Application Publication No. 2005/0204612 entitled METHOD AND DEVICE FOR PRODUCING BIODIESEL, the disclosure of which is incorporated in its entirety by reference herein. In another embodiment, the glycerol feedstock may be a hydrolysis product from a glyceride from a plant or animal source. As used herein, the terms "glycerides" and "acylglycerol" are synonymous and include mono-, di- and tri-fatty acid esters of glycerol. For example, the production of a free fatty acid product (which may be a bio-diesel) from acylglycerols, such as, for example, triacylglycerols, diacylglycerols, or monoacylglycerol, may be accompanied by the generation of a glycerol co-product which may be used as a feedstock for the present disclosure. According to one non-limiting example, the incubation of triacylglycerols with an alcohol (such as, for example, methanol) and a catalyst causes an ester-exchange reaction yielding fatty acid methyl esters and glycerol. These products may be separated into a bio-diesel-enriched product stream and a glycerol-enriched co-product stream. In certain embodiments, the glycerol-enriched co-product stream may be purified to yield food-grade or U.S.P.-grade glycerol suitable for the production of polyglycerols for use in the feed compositions of the present disclosure. In other embodiments, the glycerol-enriched co-product stream may be used directly in the feed compositions of the present disclosure or partially purified prior to use in the feed compositions. In certain embodiments, the glycerol co-product may be from a combination of the hydrolysis of glycerides from a plant or animal source and the production of a bio-diesel.

According to certain embodiments, the present disclosure comprises animal feed compositions and methods for providing dietary energy to improve health and performance of an animal. In certain embodiments, the animal feed compositions and methods may offset a reduced energy balance in the animal consuming the compositions during a time of stress. Non-limiting examples of times when an animal may be experiencing stress may include parturition; lactation; times of nutrient shortfall; changes in environmental conditions, such as, for example, changes in location, transportation, changes in temperatures or weather, and changes in feed compositions or feed patterns; times of illness; changes in social environment; or combinations of any of these. During times of stress, an animal's nutritional and dietary intake may not be sufficient to meet the metabolic needs of the animal. This may result in an energy imbalance and/or negative energy balance which may affect the health and/or performance of the animal.

Bovines, such as, dairy cattle or beef cattle, are commonly in a negative energy balance in the period surrounding calving. This energy imbalance begins immediately prior to calving and persists through the first several weeks of lactation when feed intake is insufficient to supply the energy needed to meet the metabolic requirements associated with the rapid rise in lactation and milk production. Large metabolic adjustments are required to support calving, recovery, and milk production. Productive and health concerns may arise in response to the dramatic increase in metabolic demands. Similar concerns may arise in other ruminants or mono-gastric species, where stress, as described herein, may also limit the energy supply relative to demand. As used herein, the term "ruminant" includes an even-toed hoofed animal which has a 3- or 4-chambered stomach. Non-limiting examples of ruminants include, but are not limited to, cattle (bovines), sheep (ovines), goats (caprines), oxen, musk ox, camelids (such as llamas, alpacas, and camels), cervines (such as deer and elk), and, bison. Mono-gastric animals include, but are not limited to, swine (porcines), equines, fowl, as well as domestic animals, such as, felines and canines. It is envisioned that the animal feed compositions of the present disclosure may be beneficial to ruminant and mono-gastric species of animals.

In one embodiment, the present disclosure provides a feed composition comprising feed matter and an isolated or purified polyol selected from the group consisting of an anhydro-sugar alcohol, a polyglycerol, and combinations thereof. As used herein, the terms "feed matter" or "animal feed matter" include one or more component of an animal feed and may be a wet or dry component. Non-limiting examples of feed matter or animal feed matter may include, without limitation: corn or a component of corn, such as, for example, corn meal, corn fiber, corn hulls, silage, ground corn, corn germ, corn gluten, corn oil, or any other portion of a corn plant; soy or a component of soy, such as, for example, soy oil, soy meal, soy hulls, soy silage, ground soy, or any other portion of a soy plant; wheat or any component of wheat, such as, for example, wheat meal, wheat fiber, wheat hulls, wheat chaff, ground wheat, wheat germ, or any other portion of a wheat plant; canola or any other portion of a canola plant, such as, for example, canola oil, canola meal, canola protein, canola hulls, ground canola, or any other portion of a canola plant; sunflower or a component of a sunflower plant; sorghum or a component of a sorghum plant; sugar beet or a component of a sugar beet plant; cane sugar or a component of a sugarcane plant; barley or a component of a barley plant; palm oil, palm kernel or a component of a palm plant; glycerol; corn steep liquor; a waste stream from an agricultural processing facility; lecithin; rumen protected fats; molasses; soy molasses; flax; peanuts; peas; oats; grasses, such as orchard grass and fescue, and alfalfa and/or clover used for silage or hay, and various combinations of any of the feed ingredients set forth herein.

According to certain embodiments, the feed matter may comprise at least 8% fiber by weight. According to other embodiments, the feed matter may comprise from 8% to 80% fiber by weight. In certain embodiments, at least a portion of the fiber in the feed matter may be a forage-based fiber, such as, for example alfalfa meal, alfalfa leaf meal, clover, fescue, timothy, ryegrass, orchard grass or other forage grasses, grain based forages such as corn and wheat, crop residues such as rice or wheat straw, soybean straw or corn stover, and processed by-products such as distillers grains, distillers solubles, wheat middlings, wheat bran, soy hulls, rice hulls, cottonseed hulls, corn gluten feed, corn fiber, beetpulp, citrus pulp, fruit pulps (such as, but not limited to, grape residue or apple pomace) and vegetable residues from food processing (such as, but not limited to, tomato, carrot and broccoli processing).

According to certain embodiments, the anhydro-sugar alcohol may be selected from the group consisting of sorbitan, isosorbide, anhydro-adonitol, anhydro-allitol, anhydro-altritol, anhydro-arabinitol, anhydro-ducitol (i.e., anhydro-galactitol), anhydro-erythritol, anhydro-galaxitol, anhydro-glucitol, anhydro-gulitol, anhydro-iditol, anhydro-inositol, anhydro-isomalt, anhydro-lactitol, anhydro-lyxitol, anhydro-maltitol, anhydro-mannitol, anhydro-perseitol, anhydro-ribitol, anhydro-rhamnitol, anhydro-talitol, anhydro-threitol, anhydro-xylitol, and combinations of any thereof. As defined herein, an anhydro-sugar alcohol includes the cyclic dehydration product from the dehydration of a sugar alcohol, wherein the cyclic sugar alcohol comprises at least one ring and wherein the at least one ring may be a 3-, 4-, 5-, 6-, or 7-membered cyclic ether. In certain embodiments, the anhydro-sugar alcohol may be a 5- or 6-membered cyclic ether polyol. For example, sorbitan, also known as 1,4-anhydro-D-sorbitol or 1,4-anhydro-D-glucitol is the dehydration product of sorbitol (D-glucitol) where a cyclic ether is formed between the 1- and 4-carbon of the sugar alcohol. The structure of sorbitan is represented by Structure I, below. Isosorbide (also known as 1,4:3,6-dianhydro-D-sorbitol or 1,4:3,6-dianhydro-D-glucitol), having the structure represented by Structure II, below, is the [3.3.0]bicyclic product from the dehydration of sorbitol (D-glucitol). Isosorbide may also be made by dehydration of sorbitan. Non-limiting methods for the synthesis of anhydro-sugar alcohols are disclosed in greater detail in U.S. Pat. No. 6,849,748 and U.S. Patent Application Publication No. 2004/0152907. According to certain embodiments of the present disclosure, the isolated or purified polyols do not include esters of sorbitan.

The anhydro-sugar alcohols disclosed herein and suitable for use with the various embodiments of the present disclosure may be the dehydration-cyclization product between any of the alcohol functional groups in the parent sugar alcohol backbone. For example, the term "anhydro-mannitol" includes 1,3-anhydro-mannitol, 1,4-anhydro-mannitol, 1,5-anhydro-mannitol, 1,6-anhydro-mannitol, 2,4-anhydro-mannitol, 2,5-anhydro-mannitol, 2,6-anhydro-mannitol, etc. Further, it should be understood that the anhydro-sugar alcohols disclosed herein include both enantiomeric forms of the anhydro-sugar alcohol and the racimate of the anhydro-sugar alcohol. That is, for example, the term "anhydro-mannitol" includes all anhydro-D-mannitols, all anhydro-L-mannitols and all anhydro-D,L-mannitols. Still further, the anhydro-sugar alcohols listed herein, according to the various embodiments of the present disclosure, include both the mono-dehydration products (i.e., mono-cyclic ethers) and the di-dehydration products (i.e., the bicyclic ethers).

The isolated or purified polyols of the present disclosure, such as, for example, anhydro-sugar alcohols (including, without limitation, sorbitan, and isosorbide) and polyglycerols, are distinct materials that may be stable under normal processing conditions. The isolated or purified polyols may serve as glucose precursors in the digestive tract of animals, such as, the post-rumen portions of the ruminant digestive system or the intestinal tract of mono-gastric species, and may increase the potential delivery of energy to the animal. For example, anhydro-sugar alcohols and/or polyglycerols may be substantially unfermented by the rumen microflora and pass substantially intact into the post rumen portion of the ruminant digestive tract (i.e., the intestinal tract). As used herein, the term "substantially" when used in the context of the rumen degradation of the polyol means greater than 30% by weight. In mono-gastric species, such as, for example, swine, avian species, felines, canines, and equines, anhydro-sugar alcohols and/or polyglycerols may pass substantially intact through the stomach and into the intestinal tract of the animal. Once in the intestinal tract of the animal, the anhydro-sugar alcohol and/or polyglycerols may serve as a glucose precursor and may, upon absorption, supply energy substrates (i.e., compounds that can be converted to glucose and its derivatives) to the animal. The anhydro-sugar alcohol may act as an osmotic agent within the intestine prior to absorption, altering fecal consistency, and/or reducing intestinal transit time.

In ruminants, at least a portion of the isolated or purified polyols, according to various embodiments of the present disclosure, may not be substantially fermented by the rumen microflora. For example, in vitro studies in artificial rumens show that upon in vitro fermentation of the feed compositions according to various embodiments of the present disclosure, at least a portion of the isolated or purified polyol is not substantially fermented, as demonstrated by a reduction of gas evolution in the artificial rumen environment. These studies indicated that anhydro-sugar alcohols and polyglycerols may be more resistant to rumen fermentation than glucose; sugar alcohols, such as sorbitol; and/or glycerol.

According to certain embodiments, the feed compositions of the present disclosure may be fed to many different animals. For example, according to certain embodiments, the feed compositions may be a bovine feed composition, an ovine feed composition, a caprine feed composition, an oxen feed composition, a musk ox feed composition, a camelid feed composition (i.e., a llama feed composition, an alpaca feed composition, or a camel feed composition), a cervid or deer feed composition, a bison feed composition, an avian feed composition, an equine feed composition, a canine feed composition, a feline feed composition, and/or a porcine feed composition.

According to other embodiments, the present disclosure includes an animal feed composition wherein the anhydro-sugar alcohol is selected from the group consisting of sorbitan, isosorbide, and combinations of any thereof. As discussed herein, the isolated or purified polyols may be substantially resistant to fermentation in the rumen of a ruminant or digestion in the stomach of a mono-gastric animal, and pass substantially intact into the intestinal tract of the animal.

According to certain embodiments, the animal feed composition comprises an isolated or purified polyol selected from the group consisting of sorbitan, isosorbide, a polyglycerol, and combinations of any thereof. In other embodiments, the animal feed composition may be selected from the group consisting of a bovine feed composition, an ovine feed composition, a caprine feed composition, an oxen feed composition, a musk ox feed composition, a camelid feed composition (i.e., a llama feed composition, an alpaca feed composition, or a camel feed composition), a cervid or deer feed composition, a bison feed composition, an equine feed composition, a porcine feed composition, an avian feed composition, an aquaculture feed composition, a calf or neonate feed composition, a canine feed composition, and a feline feed composition.

According to certain embodiments, the isolated or purified polyol may be included in the feed composition in an amount that provides the energy necessary or sufficient to maintain the energy balance or improve the negative energy balance of the animal, such as, for example, during a time of stress. As will be understood by one of ordinary skill in the art, the amount of isolated or purified polyol necessary to improve the energy balance may vary depending on a variety of conditions, such as, for example, the animal species, age, size, weight, diet, and/or sex; or the type of stress which the animal is experiencing, as discussed herein.

In certain embodiments, the isolated or purified polyol may comprise from 0.05% to 20% by weight of the final feed composition. According to other embodiments, the isolated or purified polyol may comprise from 0.1% to 10% by weight of the final feed composition. According to other embodiments, the isolated or purified polyol may comprise from 0.5% to 2.0% by weight of the final feed composition. According to certain embodiments wherein the feed composition is in the form of a concentrate, the isolated or purified polyol may comprise from 1% to 20% by weight of the concentrate.

The animal feed compositions of the present disclosure may be fed to an animal as part of a daily ration. The total daily amount of the isolated or purified polyol consumed as part of a daily ration by an animal will depend on various factors, as discussed herein. According to certain embodiments, for example, when the animal feeds of the present disclosure are fed to a growing or mature ruminant, the ruminant may consume from 2 g to 500 g of the isolated or purified polyol per day as part of a daily ration. According to other embodiments where the ruminant is a mature bovine, the mature bovine may consume from 10 g to 500 g of the isolated or purified polyol per day as part of a daily ration. According to certain embodiments where the ruminant is a growing bovine (i.e., a calf, the growing bovine may consume from 1 g to 40 g of the isolated or purified polyol per day as part of a daily ration. According to other embodiments wherein the ruminant is an ovine, the ovine may consume from 2 g to 150 g of the isolated or purified polyol per day as part of a daily ration.

According to other embodiments, when the animal feeds of the present disclosure may be fed to a mono-gastric animal, the mono-gastric animal may consume from 0.1 g to 500 g of the isolated or purified polyol per day as part of a daily ration. According to some embodiments where the mono-gastric animal is a swine, the swine may consume from 2 g to 250 g of the isolated or purified polyol per day as part of a daily ration. According to other embodiments where the mono-gastric animal is an equine, the equine may consume from 2 g to 500 g of the isolated or purified polyol per day as part of a daily ration. According to various embodiments where the mono-gastric animal is an avian, the avian may consume from 0.5 to 10 g of the isolated or purified polyol per day as part of a daily ration. According to certain embodiments where the mono-gastric animal is a canine, the canine may consume from 0.2 g to 100 g of the isolated or purified polyol per day as part of a daily ration. According to certain embodiments where the mono-gastric animal is a feline, the feline may consume from 0.2 g to 20 g of the isolated or purified polyol per day as part of a daily ration.

According to various embodiments of the present disclosure, the feed composition may be in any suitable form known in the animal feed art. For example, according to certain embodiments, the feed composition may be in a form selected from the group consisting of a complete feed, a feed supplement, a feed additive, a premix, a top-dress, a tub, a mineral, a meal, a block, a pellet, a mash, a liquid supplement, a drench, a bolus, a treat, and combinations of any thereof. For example, in those embodiments wherein the animal feed composition is a swine feed composition, the swine feed composition may have the form selected from the group consisting of a liquid, a pellet, a meal, and a mash.

In certain embodiments, the isolated or purified polyol may be fed directly to the animal, for example as a supplement, independent of feed matter, such as, feed dry matter (i.e., the isolated or purified polyol may be fed independent of the feed matter and prior to or after the animal consumes the feed matter.) Thus, according to various embodiments, the feed composition may comprise a supplement comprising an isolated or purified polyol selected from the group consisting of an anhydro-sugar alcohol (as set forth herein), a polyglycerol (as set forth herein), and combinations of any thereof. According to various embodiments wherein the feed composition comprises a supplement comprised of an isolated or purified polyol without additional feed matter, the feed composition/supplement may be in the form of a drench, a bolus, a treat, or a combination of any thereof.

According to other embodiments of the present disclosure, the animal feed or supplement may further comprise an ingredient selected from the group consisting of a fermentation product or by-product (such as a biomass from a yeast, bacterial or fungal fermentation), an isolated enzyme, a gluten protein, a divalent metal ion, an organic acid, an isolated or purified botanical extract, an isolated or purified capsaicin product, a mineral, a vitamin, an isolated or purified amino acid, an antibiotic, an isolated or purified sugar alcohol, and combinations of any thereof. Non-limiting examples of animal feed/supplement ingredients comprising fermentation biomasses, isolated enzymes, gluten proteins, divalent metal ions, organic acids, and/or botanical extracts are disclosed in co-pending U.S. patent application Ser. No. 11/373,681, the disclosure of which is incorporated in its entirety by reference herein. Non-limiting examples of capsaicin products and animal feeds containing capsaicin products are disclosed in U.S. Provisional Application Ser. No. 60/781,523, the disclosure of which is incorporated in its entirety by reference herein.

Further embodiments of the present disclosure describe processes for producing an animal feed composition. According to certain embodiments, a process for producing an animal feed composition according to the various embodiments disclosed herein may comprise mixing animal feed matter with an isolated or purified polyol selected from the group consisting of sorbitan, isosorbide, a polyglycerol, and combinations of any thereof to produce the animal feed composition.

According to other embodiments, the processes may further comprise forming the animal feed composition into a suitable feed form known in the art. For example, according to certain embodiments, the process may further comprise forming the animal feed composition into a form selected from the group consisting of a complete feed, a feed supplement, a feed additive, a premix, a top-dress, a tub, a mineral, a meal, a block, a pellet, a mash, a liquid supplement, a bolus, a drench, a treat, and combinations of any thereof. In various embodiments where the animal feed composition is a swine feed composition, the process may further comprise forming the swine feed composition into a form selected from the group consisting of a pellet, a meal and a mash.

According to various embodiments of the present disclosure wherein the animal feed composition is a ruminant feed composition, the isolated or purified polyol may further be an anhydro-sugar alcohol. According to certain embodiments, the process may include producing a ruminant feed composition comprising mixing animal feed matter with an isolated or purified polyol selected from the group consisting of an anhydro-sugar alcohol, a polyglycerol, and combinations thereof. In certain embodiments, the anhydro-sugar alcohol may be selected from the group consisting of sorbitan, isosorbide, anhydro-adonitol, anhydro-allitol, anhydro-altritol, anhydro-arabinitol, anhydro-ducitol (i.e., anhydro-galactitol), anhydro-erythritol, anhydro-galaxitol, anhydro-glucitol, anhydro-gulitol, anhydro-iditol, anhydro-inositol, anhydro-isomalt, anhydro-lactitol, anhydro-lyxitol, anhydro-maltitol, anhydro-mannitol, anhydro-perseitol, anhydro-ribitol, anhydro-rhamnitol, anhydro-talitol, anhydro-threitol, anhydro-xylitol, and combinations of any thereof.

In other embodiments, the process for producing an animal feed composition, as described herein, may further comprise adding an ingredient selected from the group consisting of a fermentation biomass, an isolated enzyme, a gluten protein, a divalent metal ion, an organic acid, a botanical extract, an isolated or purified capsaicin product, a mineral, a vitamin, an isolated or purified amino acid, an antibiotic, an isolated or purified sugar alcohol, and combinations of any thereof, to the animal feed composition.

According to certain embodiments, the processes for producing an animal feed composition, as described herein, may further comprise placing the feed composition or the supplement in a container which container may be configured for shipping. The processes may further comprise associating indicia with the container, such as, for example, placing or attaching graphical, written, or numerical indicia on the container. The indicia may be capable of describing the contents of the container, designating the producer of the contents, and/or directing an end user, such as, for example, a livestock producer, on how to administer the feed composition or feed supplement to the animal. According to other embodiments, the processes may further comprise shipping the container containing the feed composition or feed supplement. Any conventional method of shipping may be used, such as, for example, shipping by truck, train, ship, or plane.

According to other embodiments, the processes for producing an animal feed composition may further comprise isolating the isolated or purified polyol, producing the isolated or purified polyol, or producing and isolating the isolated or purified polyol, wherein the isolated or purified polyol may be mixed with animal feed matter to form the animal feed composition. According to certain embodiments, isolating or producing the isolated or purified polyol may comprise isolating or producing an isolated or purified polyol selected from the group consisting of sorbitan, isosorbide, a polyglycerol, anhydro-adonitol, anhydro-allitol, anhydro-altritol, anhydro-arabinitol, anhydro-ducitol (i.e., anhydro-galactitol), anhydro-erythritol, anhydro-galaxitol, anhydro-glucitol, anhydro-gulitol, anhydro-iditol, anhydro-inositol, anhydro-isomalt, anhydro-lactitol, anhydro-lyxitol, anhydro-maltitol, anhydro-mannitol, anhydro-perseitol, anhydro-ribitol, anhydro-rhamnitol, anhydro-talitol, anhydro-threitol, anhydro-xylitol, and combinations of any thereof.

According to certain embodiments, wherein the isolated or purified polyol comprises a polyglycerol, the process may further comprise producing a bio-diesel from a vegetable oil, for example by any of the methods described herein, such that monomeric glycerol is a by-product; and forming the polyglycerol from the monomeric glycerol by-product.

According to other embodiments, the present disclosure may also provide various methods of feeding an animal including, but not limited to, a ruminant. According to certain embodiments, the method of feeding an animal may comprise feeding an animal feed composition comprising an isolated or purified polyol selected from the group consisting of an anhydro-sugar alcohol, a polyglycerol, and combinations of any thereof; and animal feed matter; to the animal. According to certain embodiments, the animal may be selected from the group consisting of a bovine, an ovine, a caprine, a cervid, an oxen, a musk ox, a camelid (i.e., a llama, an alpaca, or a camel) a deer, and a bison.

According to various embodiments of the methods for feeding an animal, the animal may be lactating and the animal feed composition may be capable of at least one of increasing lactation performance, increasing milk production, increasing a milk fat content of milk, and decreasing weight loss during lactation for the lactating animal consuming the animal feed composition, as compared to a lactating animal which is not fed the animal feed composition or fed an animal feed composition which does not comprise an isolated or purified polyol selected from the group consisting of an anhydro-sugar alcohol, a polyglycerol, and combinations thereof. As used herein, the term "increased lactation performance" includes an increase in the daily amount of milk produced per the daily amount of feed consumed by the lactating animal or may also be a measure of the total volume of milk produced during lactation (which may be standardized for dairy cattle to 305 or 365 days in milk production). As used herein, the term "increased milk production" includes an increase in the volume of milk produced per day by the lactating animal. As discussed herein, the energy mobilization resulting from the production of milk during lactation may result in the loss of weight in the lactating animal due to an energy imbalance resulting from, for example, lactation. According to certain embodiments, feeding a lactating animal the animal feed composition of the present disclosure may result in a decrease in weight loss during lactation, a reduction in the incidence of health problems, metabolic disease, and/or an improvement in metabolism as observed, for example, by a decrease in blood concentration of non-esterified fatty acids ("NEFA"), ketones, and/or beta-hydroxy butyric acid ("BHBA"), and/or decrease in liver fat content (liver triglyceride concentration). According to still other embodiments, feeding the animal feed compositions of the present disclosure to animals, such as, lactating animals, may improve reproductive efficiency (i.e., reduced time of return to estrus, improved conception rate, increased health of offspring, decrease weight loss during pregnancy, etc.).

According to certain embodiments, the method of feeding an animal may further comprise mixing animal feed matter with an isolated or purified polyol selected from the group consisting of an anhydro-sugar alcohol, a polyglycerol, and combinations of any thereof to form an animal feed composition. In certain embodiments, the method may comprise mixing an animal feed supplement comprising a concentrated form of the isolated or purified polyol with the animal feed matter. The concentrated form of the isolated or purified polyol may be either in a liquid form, such as, for example, a concentrated aqueous solution, or a solid form. According to various embodiments, the isolated or purified polyol may be fed to the ruminant at a concentration of 0.05% to 20% by weight of the animal feed composition.

Other embodiments of the present disclosure describe a method of improving energy balance in an animal during a time of stress. The method may comprise feeding the animal a feed composition according to any of the various embodiments disclosed herein during the time of stress. As used herein, "times of stress" includes, but are not limited to, changes in environment or health, such as, for example, during pregnancy and the period around parturition (up to 4 weeks prior and 8 weeks post parturition, as for example in a lactating ruminant), times of nutrient shortfall, illness, changes in social environment, and changes in environmental conditions, for example, changes in location, transportation, increases or decreases in temperature or other changes in weather conditions (such as, for example, increased humidity, or storms), changes in feed composition.

According to other embodiments, the present disclosure describes methods of supplementing a diet of an animal. Supplementing the diet of an animal may comprise feeding the animal a feed supplement comprising an isolated or purified polyol selected from the group consisting of an anhydro-sugar alcohol, a polyglycerol, and combinations of any thereof. As described herein, the supplement may comprise the isolated or purified polyol and be substantially free of other feed matter, such as feed dry matter. In other embodiments, the supplement may further include one or more of vitamins, minerals, divalent metal ions, botanical extracts, medicaments (such as an antibiotic), fermentation biomasses, isolated enzymes, gluten proteins, organic acids, an isolated or purified capsaicin product, an isolated or purified amino acid, and combinations of any thereof. According to various embodiments, the feed supplement may be in a form selected from the group consisting of a bolus, a drench, and a treat.

In certain embodiments of the present disclosure, an animal feed composition may comprise feed matter and an isolated or purified sorbitan, an isolated or purified polyglycerol, or a combination thereof. For a ruminant fed a restricted diet, a circulating level of non-esterified fatty acids in the ruminant's blood may decrease after three hours upon administration of the animal feed composition, described herein. In other embodiments, the animal feed composition described herein may comprise isolated or purified sorbitan, isolated or purified polyglycerol, or the combination thereof. The isolated or purified sorbitan, the isolated or purified polyglycerol, or the combination thereof may comprise from 0.05% to 20% by weight of the animal feed composition. The isolated or purified sorbitan, the isolated or purified polyglycerol, or the combination thereof may comprise from 0.1% to 10% by weight of the animal feed composition. The isolated or purified sorbitan, the isolated or purified polyglycerol, or the combination thereof may comprise from 0.05% to 2% by weight of the animal feed composition. In other embodiments, upon placement of the animal feed composition in contact with rumen fluid for twenty four hours, a quantity of gas produced by fermentation of 0.3 grams of the isolated or purified sorbitan, the isolated or purified polyglycerol, or the combination thereof may be less then fifty milliliters. In other embodiments, the feed matter may be selected from the group consisting of a corn product, a soybean product, a vitamin, a mineral, an isolated or purified amino acid, a fat, hay, a fermentation by-product, a wheat product, a canola product, and combinations of any thereof. In other embodiments, upon placement of the animal feed composition in contact with rumen fluid for twenty four hours, a quantity of gas produced by fermentation of 0.3 grams of the isolated or purified sorbitan, isolated or purified polyglycerol, or the combination thereof may be less than twenty milliliters.

The various embodiments of the present disclosure will be better understood when read in conjunction with the following non-limiting Examples.

EXAMPLES

Example 1

In this Example, the fermentation of glucose, sorbitol, glycerol, sorbitan and polyglycerols in an artificial rumen environment was evaluated. Fermentations were performed on two separate days where gas production was monitored every 30 minutes. In addition, pH, ammonia ($NH_3$), and volatile fatty acid ("VFA") production were measured after 24 hours. Duplicate samples of each compound were evaluated using in vitro rumen fermentations. The results of the in vitro study are presented in Table 1.

The fermentation of glucose, sorbitol, sorbitan, glycerol, polyglycerol 4 (PG4), and polyglycerol 8 (PG8) was examined. Duplicate samples of these compounds were fermented in vitro using rumen fluid as inoculum. Samples were weighed into 150 mL serum bottles (0.3 grams per bottle) using a $CO_2$ atmosphere to provide an anaerobic environment. A standard buffered media was prepared (no additional feed matter was included in the fermentation), degassed, and added to the serum bottles (see, Goering, H. K., and P. J. Van Soest, "Forage Fiber Analyses (Apparatus, Reagents, Procedures, and Some Applications)," *Agric. Handbook*, No 379, ARS-USDA, Washington, D.C., 1970). Rumen fluid was obtained from a dairy cow, filtered, and added to the serum bottles as 20% of the total fluid addition (30 mL total fluid volume). The serum bottles were sealed, placed in an incubator, and the fermentation was allowed to proceed. Fermentations were performed on two separate days, during which time gas production was monitored every 30 minutes and pH, $NH_3$, and VFA production measured after 24 hours.

Figure 1:
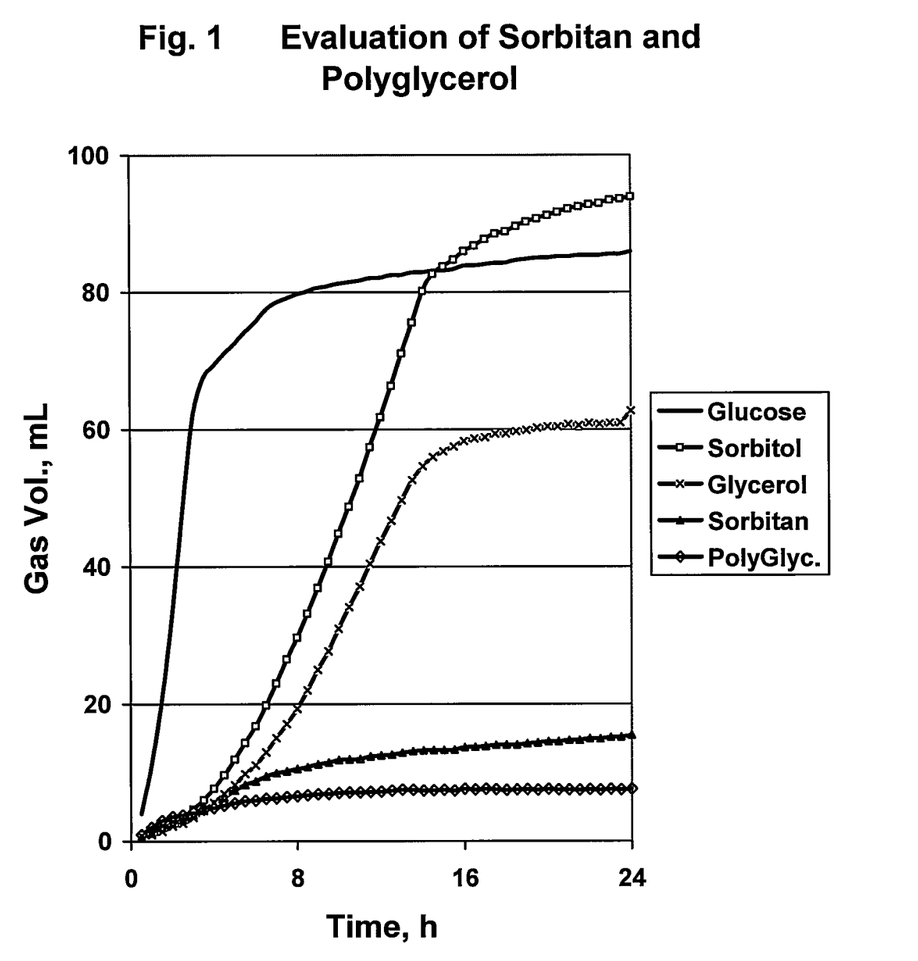
FIG. 1 illustrates in vitro gas evolution over time of various embodiments of polyol ingredients of the present disclosure compared to other additives.

The fermentation rate for sorbitol was slower than glucose, but final gas volume and VFA concentration suggest it was largely fermented by 24 hours. Glycerol also fermented at a slow rate; however, the high levels of propionate suggest gas production would be lower than typical carbohydrates and that glycerol is also largely fermented by 24 hours. The fermentation rates of sorbitan and the polyglycerols were slower than glucose, sorbitol, or glycerol, with low gas and VFA production and minimal effects on ammonia concentration. As shown in FIG. 1, fermentation proceeds much more slowly and to a lesser extent for sorbitan and the polyglycerols than sorbitol or glycerol. Based on the rate of fermentations, the rumen escape for sorbitol and glycerol may be estimated to be between 30 and 50%. That is, between 30% and 50%, by weight, of the sorbitol or glycerol would escape fermentation in the rumen. In contrast, sorbitan and the polyglycerols produced less than 20% of the gas observed from the original sugar, even at the end of 24 hours, and therefore is estimated to have greater than 80% rumen escape.

TABLE 1

In Vitro Results From The Fermentation Of Polyols

|  | Glucose | Sorbitol | Glycerol | Sorbitan | PG4 | PG8 |
| --- | --- | --- | --- | --- | --- | --- |
| pH | 5.81 | 6.00 | 6.12 | 6.65 | 6.7 | 6.68 |
| Gas 24 h, mL/0.3 g | 78.5 | 87.6 | 56.5 | 15.5 | 7.6 | 7.6 |

TABLE 1-continued

In Vitro Results From The Fermentation Of Polyols

|  | Glucose | Sorbitol | Glycerol | Sorbitan | PG4 | PG8 |
| --- | --- | --- | --- | --- | --- | --- |
| $NH_3$, mg/dL | 26.4 | 30.2 | 37.2 | 59.1 | 57.2 | 58.2 |
| Acetate mM | 28.4 | 18.2 | 3.1 | 4.0 | 2.1 | 2.2 |
| Propionate, mM | 18.2 | 10.5 | 36.9 | 1.2 | 1.0 | 1.0 |
| Total Butyrate[1], mM | 10.8 | 17.8 | 8.8 | 3.7 | 1.2 | 0.7 |
| Total VFA[1], mM | 55.2 | 45.2 | 47.5 | 8.0 | 3.0 | 2.4 |
| Acetate, % VFA | 51.4 | 40.3 | 6.5 | 50.0 | 70.0 | 91.7 |
| Propionate, % VFA | 33.0 | 23.2 | 77.7 | 15.0 | 33.3 | 41.7 |
| Tot Butyrate, % VFA | 19.6 | 39.4 | 18.5 | 46.3 | 40.0 | 29.2 |

[1]Total butyrate = n-butyrate + isobutyrate, Total VFA = acetate + propionate + butyrate.

Example 2

Ruminant Feed Composition

In this Example, a feed composition for ruminants, such as cattle, is mixed. The ruminant feed composition is a combination of feeds made on-site (for example, on a farm) and in a manufacturing facility. Specifically, the ruminant feed composition includes a concentrate portion produced at a first location (i.e., a manufacturing facility) that is added to animal feed matter at a second location (i.e., the site where the animals are kept).

The composition of the concentrate is presented in Table 2. The ingredients are blended by adding ingredients to a large mixer and either grinding the ingredients into a meal feed, or grinding the ingredients and forming the ground ingredients into a pellet to produce the concentrate. This concentrate may be delivered to location in bulk and stored until use or the concentrate may be delivered to a location in bags where it may be stored until use.

The ingredients of the animal feed composition are listed in Table 3. The ingredients in Table 3 may be blended on-site, for example, in a large mixer, and the resulting feed composition may be fed to the ruminant as a total mixed ration. In a smaller farm situation, the user may mix several of the ingredients and deliver specific amounts of the animal feed composition to particular ruminants.

TABLE 2

Composition Of Concentrate Treatment

| Ingredients, | Dry Matter (DM) % by weight |
| --- | --- |
| Corn, ground | 52.50 |
| Starches | 7.28 |
| Soybean Meal | 14.93 |
| Vitamins and Minerals | 8.02 |
| Amino Acids | 2.51 |
| Magnesium Oxide | 3.20 |
| Fat | 2.21 |
| Molasses | 2.00 |
| Sorbitan or Polyglycerol | 7.35 |
| Total | 100.00 |

TABLE 3

Composition Of Ruminant Diet

| Ingredients, | DM % by weight |
| --- | --- |
| Corn Silage, | 40.00 |
| Timothy Hay | 28.65 |
| Concentrate Treatment | 12.00 |
| Western Hay | 10.35 |
| Wet Brewer's Grain | 5.00 |
| Soyhull Pellets | 4.00 |
| Total | 100.00 |

Example 3-Mono-Gastric Feed Composition

In this Example, a feed composition for mono-gastric mammals, such as swine, is mixed. The animal feed composition is a combination of ingredients that may be added to a mixer, usually at a manufacturing facility or using a mill located on-site. The ingredients may be mixed and ground into a meal or a mash feed. The meal or mash may be offered to the mono-gastric animal as a total mixed ration. Table 4 lists the ingredients of a diet useful for feeding swine.

TABLE 4

Composition Of Swine Diet

| Ingredients, | DM % by weight |
| --- | --- |
| Corn, ground | 55.90 |
| Wheat Middlings | 15.00 |
| 47.5% Soybean Meal | 13.06 |
| Soy Hulls | 10.09 |
| Vitamins and Minerals | 4.95 |
| Sorbitan or Polyglycerol | 1.00 |
| Total | 100.00 |

Example 4

In this Example, the effect of a diet comprising an isolated or purified polyol on the level of circulating non-esterified fatty acids ("NEFA") in lambs was examined.

Four lambs were used in this Example. The lambs were fed a basal diet the first week followed by at least 4 weeks during which the supplement treatments were evaluated. The lambs were fed a diet supplement comprising sorbitan during the second and third weeks of the treatment. The lambs were fed a diet supplement comprising polyglycerol during the fourth and fifth weeks of the treatment. The diet supplements were fed separate from the basal diet feed. Table 5 lists the ingredients of the basal diet fed the lambs.

TABLE 5

Composition of Lamb Diets
Ingredient Basis: Dry Matter % by weight

| Corn Grain Cracked | 32.56 |
| --- | --- |
| Molasses-Cane | 2.66 |
| Chopped Grass Hay | 13.95 |
| Dist. Dried Grains & Solubles | 29.90 |
| Soybean Hulls | 14.95 |
| 36% Sheep Concentrate | 4.98 |
| Calcium Carbonate | 1.00 |
| Total | 100.00 |

Supplements were administered at the beginning of the third day of weeks 2-5 with a dose of 25 grams supplement/lamb to 45 grams supplement/lamb. In week two, lambs 1 and 2 were fed a full feed diet for all 7 days with administration of the sorbitan supplement on day 3, while lambs 3 and 4 were fed a restricted diet at 75% of maintenance energy requirements for 3 days, then fed a full feed diet for the 4 days after administration of the sorbitan supplement. In week three, lambs 3 and 4 were fed a full feed diet for all 7 days with administration of the sorbitan supplement on day 3, while lambs 1 and 2 were fed a restricted diet at 75% of maintenance energy requirements for 3 days then, fed a full feed diet for the 4 days after administration of the sorbitan supplement. In week four, lambs 1 and 2 were fed a full feed diet for all 7 days with administration of the polyglycerol supplement on day 3, while lambs 3 and 4 were fed a restricted diet at 75% of maintenance energy requirements for 3 days, then fed a full feed diet for the 4 days after administration of the polyglycerol supplement. In week five, lambs 3 and 4 were fed a full feed diet for all 7 days with administration of the polyglycerol supplement on day 3, while lambs 1 and 2 were fed a restricted diet at 75% of maintenance energy requirements for 3 days then fed a full feed diet for the 4 days after administration of the polyglycerol supplement. Therefore, each lamb consumed sorbitan and polyglycerol with full feed and with feed restriction during the study.

Figure 2:
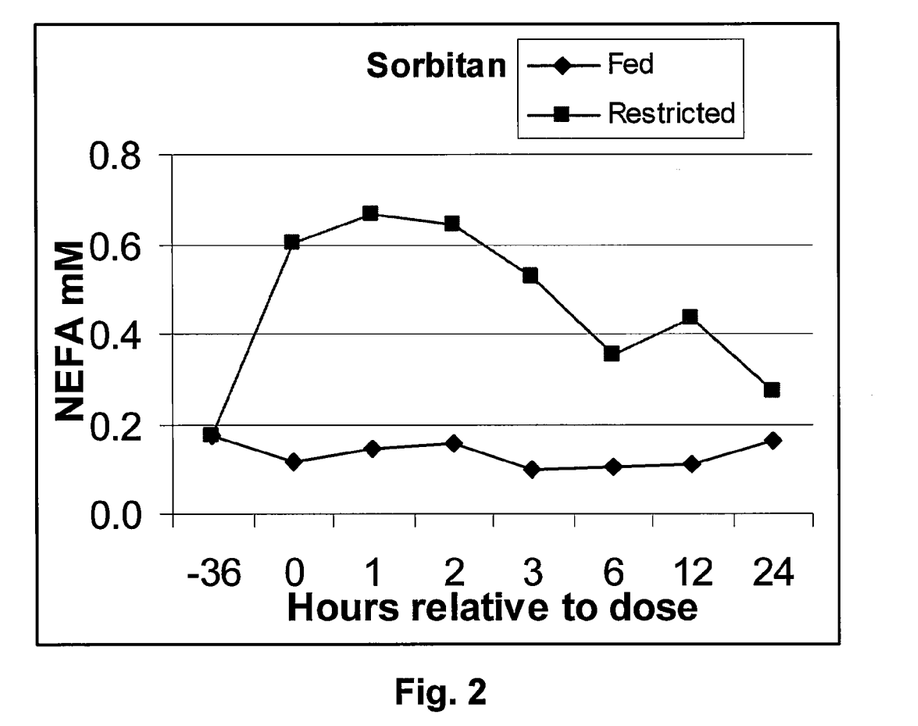
FIG. 2 illustrates circulating non-esterified fatty acid ("NEFA") content in lambs fed a supplement comprising sorbitan.
Figure 3:
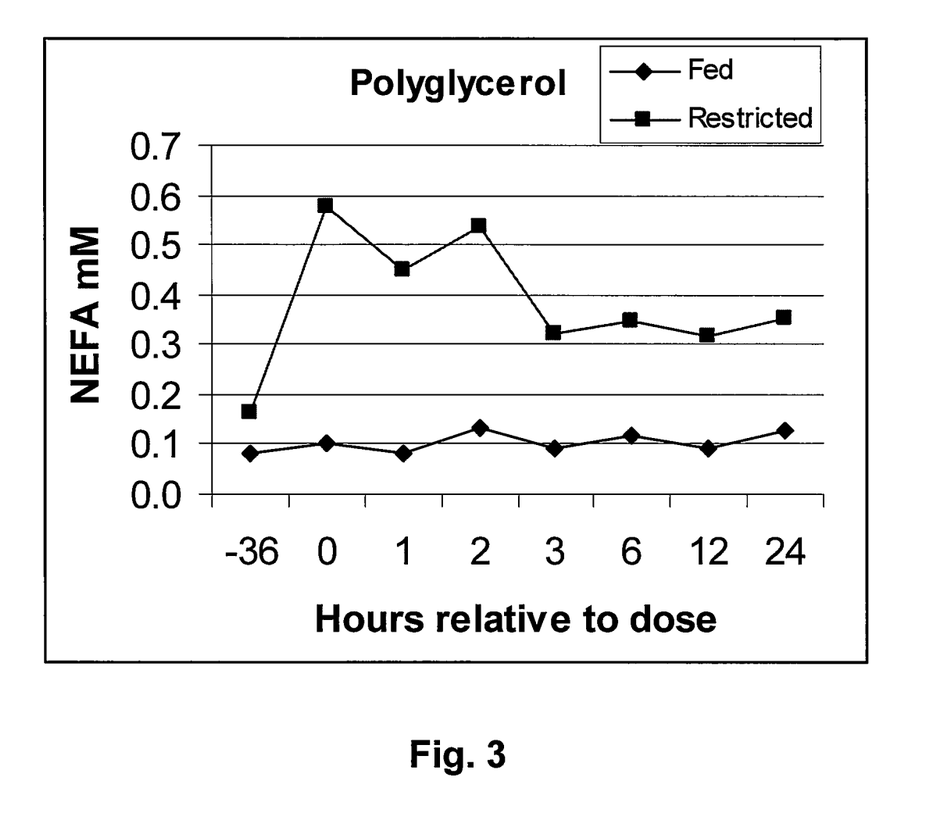
FIG. 3 illustrates circulating NEFA content in lambs fed a supplement comprising polyglycerol.

Blood, fecal and urine samples collected immediately prior to (−36 hours relative to dose) and after the dose (1, 2, 3, 6, 12, and 24 hours relative to dose) were measured for content of sorbitan or polyglycerol, glucose, non-esterified fatty acids (NEFA) and beta-hydroxybutyrate (BHBA) concentration. Average change in NEFA content in the blood for animals (restricted diet, 75% of maintenance energy requirements, and normal diet) fed the supplement comprising sorbitan are illustrated in FIG. 2. Average change in NEFA content in the blood for animals (restricted diet, 75% of maintenance energy requirements, and normal diet) fed the supplement comprising polyglycerol are illustrated in FIG. 3. Blood concentrations of NEFA increased in the lambs in response to feed restriction. The addition of sorbitan or polyglycerol to the diet led to a decrease in circulating NEFA levels in the lambs fed the restricted diet, which occurred independent to feed intake, indicating the potential to offset the negative energy balance experienced by these lambs.

Although the foregoing description has presented a number of exemplary embodiments of the invention, those of ordinary skill in the relevant art will appreciate that various changes in the components, details, materials, and process parameters of the examples that have been herein described and illustrated in order to explain the nature of the invention may be made by those skilled in the art, and all such modifications will remain within the principle and scope of the invention as expressed herein in the appended claims. It will also be appreciated by those skilled in the art that changes could be made to the embodiments described above without departing from the broad inventive concept thereof. It is understood, therefore, that this invention is not limited to the particular embodiments disclosed, but it is intended to cover modifications and/or combinations of various feed ingredients that are within the principle and scope of the invention, as defined by the claims.

We claim:

1. A method of providing dietary energy to a ruminant, comprising:
feeding an animal feed composition comprising a metabolically effective amount of an oligomeric and/or polymeric chain of monomeric glycerol ($HOCH_2CH(OH)$ CH$_2$OH) bonded by ether linkages at a hydroxyl residue of the monomeric glycerol and animal feed matter to the ruminant.

2. The method of claim 1, wherein the ruminant is lactating and the animal feed composition is capable of at least one of increasing lactation performance, increasing milk production, increasing a milk fat content of milk, decreasing weight loss during lactation, reducing the incidence of metabolic disease, improving reproductive efficiency, reducing blood concentrations of at least one of non-esterified fatty acids, and beta-hydroxy butyric acid, and reducing liver triglyceride concentrations, as compared to a lactating ruminant which is not fed the animal feed composition.

3. The method of claim 1, wherein upon feeding of the animal feed composition to the ruminant, a circulating level of non-esterified fatty acids in the ruminant's blood decreases after three hours.

4. The method of claim 1, wherein the ruminant is selected from the group consisting of a bovine, an ovine, a caprine, an oxen, a musk ox, a cervid, a deer, a bison, and a camelid.

5. The method of claim 1, further comprising mixing an animal feed supplement comprising a concentrated form of the oligomeric and/or polymeric chain of the monomeric glycerol (HOCH$_2$CH(OH)CH$_2$OH) bonded by ether linkages at the hydroxyl residue of the monomeric glycerol with the animal feed matter.

6. The method of claim 1, wherein the oligomeric and/or polymeric chain of the monomeric glycerol (HOCH$_2$CH(OH)CH$_2$OH) bonded by ether linkages at the hydroxyl residue of the monomeric glycerol is fed to the animal at a concentration of 0.05% to 20% by weight of the animal feed composition.

7. The method of claim 1, wherein the animal feed composition is in a form selected from the group consisting of a bolus, a drench, and a treat.

8. The method of claim 1, further comprising mixing a fermentation by-product with the animal feed composition.

9. The method of claim 1, wherein the animal feed matter comprises between 8-80% fiber by weight.

10. The method of claim 1, wherein the animal feed composition further comprises isosorbide.

11. A method of providing dietary energy to a bovine, comprising:
    mixing a metabolically effective amount of an oligomeric and/or polymeric chain of monomeric glycerol (HOCH$_2$CH(OH)CH$_2$OH) bonded by ether linkages at a hydroxyl residue of the monomeric glycerol with feed matter, thus producing an animal feed composition; and
    feeding the animal feed composition to the bovine in an amount such that the bovine receives between 2 grams and 500 grams of the isolated or purified polyglycerol per day.

12. The method of claim 11, wherein the bovine is lactating.

13. The method of claim 11, further comprising mixing a fermentation by-product with the animal feed composition.

14. The method of claim 11, further comprising mixing an isolated or purified 1,4-anhydro-D-sorbitol with the feed matter.

15. The method of claim 11, wherein the feed matter comprises between 8-80% fiber by weight.

16. The method of claim 11, further comprising mixing a botanical with the animal feed composition.

* * * * *